(12) United States Patent
Xu (10) Patent No.: US 10,591,445 B2
(45) Date of Patent: Mar. 17, 2020

(54) METHODS FOR ANALYSIS AND RESOLUTION OF PREPARATIONS OF DIANHYDROGALACTITOL AND DERIVATIVES OR ANALOGS THEREOF

(71) Applicant: Del Mar Pharmaceuticals (BC) Ltd., Vancouver (CA)

(72) Inventor: Qiang Xu, Menlo Park, CA (US)

(73) Assignee: Del Mar Pharmaceuticals (BC) Ltd., Vancouver (CA)

( * ) Notice: Subject to any disclaimer, the term of this patent is extended or adjusted under 35 U.S.C. 154(b) by 104 days.

(21) Appl. No.: 15/778,546

(22) PCT Filed: Nov. 22, 2016

(86) PCT No.: PCT/US2016/063362
§ 371 (c)(1),
(2) Date: May 23, 2018

(87) PCT Pub. No.: WO2017/091588
PCT Pub. Date: Jun. 1, 2017

(65) Prior Publication Data
US 2018/0284077 A1    Oct. 4, 2018

Related U.S. Application Data

(60) Provisional application No. 62/260,019, filed on Nov. 25, 2015.

(51) Int. Cl.
*G01N 30/22* (2006.01)
*C07D 303/14* (2006.01)
(Continued)

(52) U.S. Cl.
CPC ........... *G01N 30/22* (2013.01); *C07D 303/14* (2013.01); *G01N 30/74* (2013.01); *G01N 30/88* (2013.01);
(Continued)

(58) Field of Classification Search
None
See application file for complete search history.

(56) References Cited

U.S. PATENT DOCUMENTS 9,029,164 B2   5/2015   Lu et al.
9,759,698 B2   9/2017   Liu
(Continued)

FOREIGN PATENT DOCUMENTS

WO   2012/024368 A2   2/2012
WO   2013/128285 A2   9/2013
WO   2015/074025 A1   5/2015

OTHER PUBLICATIONS

Extended European Search Report dated Jul. 12, 2019, issued in corresponding European Application No. 16869177.2, filed Nov. 22, 2016, 6 pages.
(Continued)

Primary Examiner — Xiaoyun R Xu
(74) Attorney, Agent, or Firm — Christensen O'Connor Johnson Kindness PLLC (57) ABSTRACT

An improved analytical method for analysis of dianhydrogalactitol preparations provides a method for determining the purity of dianhydrogalactitol and detecting impurities in preparations of dianhydrogalactitol, as well as identifying any such impurities. The method employs high performance liquid chromatography (HPLC), in particular, HPLC employing a reverse phase amide column with ELSD detection; the HPLC can be followed by tandem mass spectroscopy. The method can further comprise the step of performing preparative HPLC collection of at least one specific substance peak present in a preparation of dianhydrogalactitol.

20 Claims, 5 Drawing Sheets

(51) Int. Cl.
*G01N 30/74* (2006.01)
*G01N 30/88* (2006.01)
G01N 30/30 (2006.01)
G01N 30/72 (2006.01)
G01N 30/02 (2006.01)
G01N 30/32 (2006.01)
B01D 15/30 (2006.01)
G01N 30/34 (2006.01)

(52) U.S. Cl.
CPC ............ *B01D 15/305* (2013.01); *G01N 30/30* (2013.01); *G01N 30/34* (2013.01); *G01N 30/7233* (2013.01); *G01N 2030/027* (2013.01); *G01N 2030/324* (2013.01); *G01N 2030/8872* (2013.01)

(56) References Cited

U.S. PATENT DOCUMENTS

| | | |
|---|---|---|
| 2010/0285603 A1 | 11/2010 | Kobold et al. |
| 2014/0017798 A1 | 1/2014 | Yu |
| 2014/0193855 A1 | 7/2014 | Agris et al. |
| 2014/0306105 A1 | 10/2014 | Netto et al. |
| 2014/0315318 A1 | 10/2014 | Lu et al. |
| 2015/0027206 A1 | 1/2015 | Lu |
| 2015/0074025 A1 | 3/2015 | Chien et al. |

OTHER PUBLICATIONS

Ares, A.M., et al., "Hydrophilic Interaction Chromatography in Drug Analysis," Central European Journal of Chemistry, 10(3):534-553, Feb. 2012.

Lurie, I.S., et al., "Hydrophilic Interaction Chromatography of Seized Drugs and Related Compounds with Sub 2 μm Particle Columns," Journal of Chromatography A 1218(52):9336-9344, Oct. 2011.

Ruta, J., et al., "Method Development for Pharmaceutics: Some Solutions for Tuning Selectivity in Reversed Phase and Hydrophilic Interaction Liquid Chromatography," Journal of Pharmaceutical and Biomedical Analysis 63(9):95-105, Jan. 2012.

"2424 Evaporative Light Scattering Detector," Operator's Guide, Document No. 71500121802/Revision B, Waters Corporation, Manchester, U.K., ©2006-2009, 196 pages.

Bartos, D., and S. Görög, "Recent Advances in the Impurity Profiling of Drugs," Current Pharmaceutical Analysis 4(4):215-230, Nov. 2008.

"Bioseparation: From Microanalysis to Plant-Scale Purification," YMC Co., Ltd., Kyoto, Japan, © 2015, 24 pages.

Guzzetta, A., "Reverse Phase HPLC Basics for LC/MS," IonSource, Jul. 22, 2001 <http://ionsource.com/tutorial/chromatography/rphplc.htm> [retrieved May 30, 2018], 9 pages.

International Search Report and Written Opinion dated Dec. 20, 2013 (corrected version), issued in corresponding International Application No. PCT/IB2013/000793, filed Feb. 26, 2013, 9 pages.

International Search Report and Written Opinion dated Mar. 4, 2015, issued in corresponding International Application No. PCT/US2014/066087, filed Nov. 18, 2014, 9 pages.

International Search Report dated Feb. 16, 2017, issued in corresponding International Application No. PCT/US2016/063362, filed Nov. 22, 2016, 2 pages.

Lantz, M.D., et al., "Simultaneous Resolution and Detection of a Drug Substance, Impurities, and Counter Ion Using a Mixed-Mode HPLC Column With Evaporative Light Scattering Detection," Journal of Liquid Chromatography & Related Technologies 20(9):1409-1422, 1997.

Rao, R.N., and V. Nagaraju, "An Overview of the Recent Trends in Development of HPLC Methods for Determination of Impurities in Drugs," Journal of Pharmaceutical and Biomedical Analysis 33(3):335-377, Oct. 2003.

U.S. Food and Drug Administration, "Guidance for Industry: Q2B Validation of Analytical Procedures: Methodology," Nov. 1996, 13 pages.

Ross, E., "Waters Amide Column Technology for Food Analysis," Waters Corporation, 2012, 53 pages.

International Preliminary Report on Patentability dated Aug. 23, 2018, in corresponding International Application No. PCT/US2016/063362, filed Nov. 22, 2016, 36 pages.

METHODS FOR ANALYSIS AND RESOLUTION OF PREPARATIONS OF DIANHYDROGALACTITOL AND DERIVATIVES OR ANALOGS THEREOF

CROSS-REFERENCE TO RELATED APPLICATION

This application is a national phase of International Application No. PCT/US2016/063362, filed Nov. 22, 2016, which claims the benefit of United States Provisional Application No. 62/260,019, filed Nov. 25, 2015, the contents of which are incorporated herein in their entirety by this reference.

FIELD OF THE INVENTION

This invention is directed to improved analytical methods for dianhydrogalactitol and derivatives or analogs thereof, especially involving high performance liquid chromatography (HPLC).

BACKGROUND OF THE INVENTION

Dianhydrogalactitol (1,2:5,6 dianhydrogalactitol or DAG) is one of a number of hexitols or hexitol derivatives having significant pharmacological activity, including chemotherapeutic activity. In particular, dianhydrogalactitol has been suggested for use in chemotherapy, such as in U.S. Pat. No. 7,157,079 to Nielsen et al., incorporated herein by this reference.

Dianhydrogalactitol has activity against a number of neoplasms. However, if dianhydrogalactitol is to be used successfully as a therapeutic agent, an extremely high degree of purity and the removal of impurities is essential. The presence of impurities can lead to undesirable side effects. One example occurred a number of years ago, when impurities present in a batch of the amino acid tryptophan, a normal constituent of protein, were responsible for a significant outbreak of eosinophilia-myalgia syndrome, which caused a large number of cases of permanent disability and at least 37 deaths. This is particularly important if the therapeutic agent such as dianhydrogalactitol is to be employed in patients with compromised immune systems or liver or kidney dysfunction, or in elderly patients. Such patients may experience a greater incidence of undesirable side effects owing to their sensitivity to contaminants.

One of the impurities found in preparations of dianhydrogalactitol is dulcitol. Other impurities exist in preparations of dianhydrogalactitol as well, depending on their method of preparation.

Therefore, there is a need for improved analytical methods to detect impurities and degradation products in preparations of dianhydrogalactitol to provide preparations of greater purity that are less likely to induce side effects when dianhydrogalactitol is administered for therapeutic purposes.

SUMMARY OF THE INVENTION

An improved analytical method for determining the purity of dianhydrogalactitol and derivatives or analogs thereof and detecting impurities and degradation products in preparations of dianhydrogalactitol and derivatives or analogs thereof that meets these needs is described herein. In particular, the analytical method is suitable for determining the purity of dianhydrogalactitol and detecting impurities and degradation products in preparations of dianhydrogalactitol.

In general, this analytical method employs high performance liquid chromatography (HPLC), in particular, HPLC with evaporative light scattering detection (ELSD).

In particular, an analytical method according to the present invention can detect the impurities dulcitol and dibromodulcitol in a preparation of dianhydrogalactitol.

One aspect of the present invention is an analytical method for analyzing the presence and quantity of impurities present in a preparation of dianhydrogalactitol comprising the steps of:

(1) analyzing a preparation of dianhydrogalactitol by subjecting the preparation to high performance liquid chromatography using a reversed phase amide column employing amide chemistry in a hydrophilic interaction mode and ethylene bridged hybrid (BEH) technology with elution with a mobile phase gradient wherein a first mobile phase is 100% acetonitrile and a second mobile phase is 100% water to separate dianhydrogalactitol from dulcitol and other contaminants of the preparation; and (2) determining the relative concentration of one or more peaks resolved by high performance liquid chromatography that represent compounds other than dianhydrogalactitol itself.

Typically, the method detects and quantitates at least one of: (1) dulcitol; (2) dibromodulcitol; (3) an impurity other than dulcitol; and (4) a degradation product of dianhydrogalactitol.

Typically, the flow rate is from about 0.72 mL/min to about 0.88 mL/min. Preferably, the flow rate is about 0.80 mL/min.

Typically, the scheme for elution is (1) 0.00 minutes, 90% of 100% acetonitrile; 10% of 100% water; (2) 3.00 minutes, 90% of 100% acetonitrile; 10% of 100% water; (3) 20.00 minutes, 75% of 100% acetonitrile, 25% of 100% water; (4) 25.00 minutes, 50% of 100% acetonitrile, 50% of 100% water; (5) 30.00 minutes, 50% of 100% acetonitrile, 50% of 100% water; (6) 30.10 minutes, 90% of 100% acetonitrile, 10% of 100% water; and (7) 40.00 minutes, 90% of 100% acetonitrile, 10% of 100% water.

Typically, the injection volume is from about 154 to about 35 µL. Preferably, the injection volume is about 25 µL.

Typically, the column temperature is from about 28° C. to about 32° C. Preferably, the column temperature is about 30° C.

Typically, the run time is about 40 minutes.

In one alternative, the injector temperature is at about 5° C. In another alternative, the injector temperature is at about 20° C. to about 22° C.

The method can include a needle wash with 100% acetonitrile.

In a method according to the present invention, typically, detection is by means of evaporative light scattering (ELSD). Typically, the evaporative light scattering detection comprises post-column addition of a volatile solvent to enhance evaporation of the aqueous fraction of any mobile phase present. The volatile solvent can be selected from the group consisting of methanol, ethanol, isopropanol, and acetonitrile. In one preferred alternative, the ELSD detection conditions are a temperature from about 36° C. to about 44° C., a gas pressure from about 2.0 bar to about 3.0 bar, and a gain of 7. In a more preferred alternative, the ELSD conditions are a temperature from about 38° C. to about 42° C., a gas pressure from about 2.25 bar to about 2.75 bar, and a gain of 7. In a still more preferred alternative, the ELSD conditions are a temperature of about 40° C., a gas pressure of about 2.5 bar, and a gain of 7. The evaporative light scattering detection can be compatible with electrospray LC/MS. When the evaporative light scattering detection is compatible with electrospray LC/MS, an electrospray tandem mass spectrometer can be installed and connected on-line to an HPLC system with ELSD. When an electrospray tandem mass spectrometer is installed and connected on-line, tandem mass spectral data providing chemical information for each of the impurities and degradation products that may be present in a preparation of dianhydrogalactitol can be collected. The mass spectroscopy in tandem with HPLC can provide molecular ion information and possible chemical structures having a molecular weight consistent with the molecular ion information for each of the observed impurities and degradation products. In this alternative, at least one impurity or degradation product is identified by separation by column chromatography followed by at least one purification procedure to yield a solid unknown sample. The solid unknown sample can be characterized for identification by at least one standard analytical procedure selected from the group consisting of nuclear magnetic resonance (NMR), mass spectroscopy (MS), Fourier transform infrared spectroscopy (FT-IR), elemental analysis, determination of purity by HPLC, and determination of water content by the Karl Fischer titration method.

In the method as described above, the method can further comprise the step of performing preparative HPLC collection of at least one specific substance peak present in a preparation of dianhydrogalactitol. The at least one specific substance peak present in the preparation of dianhydrogalactitol can be an impurity. Alternatively, the at least one specific substance peak present in the preparation of dianhydrogalactitol can be a degradation product.

BRIEF DESCRIPTION OF THE DRAWINGS

These and other features, aspects, and advantages of the present invention will become better understood with reference to the following description, appended claims, and accompanying drawings where:

DETAILED DESCRIPTION OF THE INVENTION

This invention is directed to improved analytical methods for determining the purity of dianhydrogalactitol and derivatives or analogs thereof and determining the existence and concentration of impurities present in preparations of dianhydrogalactitol and derivatives or analogs thereof. An improved analytical method for determining the purity of dianhydrogalactitol and derivatives or analogs thereof and detecting impurities and degradation products in preparations of dianhydrogalactitol and derivatives or analogs thereof that meets these needs is described herein. In particular, the analytical method is suitable for determining the purity of dianhydrogalactitol and detecting impurities and degradation products in preparations of dianhydrogalactitol.

The structure of dianhydrogalactitol is shown below as Formula (I):

One of the significant impurities present in dianhydrogalactitol preparations is dulcitol. The structure of dulcitol is shown below in Formula (II).

Yet another impurity that can be present in dianhydrogalactitol preparations is dibromodulcitol. The structure of dibromodulcitol is shown below in Formula (III).

Other impurities can be present in preparations of dianhydrogalactitol. The exact identity of such impurities can depend on the routes of synthesis and purification for dianhydrogalactitol. Such impurities can also represent degradation products of dianhydrogalactitol.

An improved method of analyzing dianhydrogalactitol preparations is based on HPLC (high performance liquid chromatography) with evaporative light scattering detection (ELSD). In one alternative, to detect and identify all significant components present in such dianhydrogalactitol preparations, HPLC is combined with mass spectroscopy (MS).

The theory and practice of HPLC are described in L. R. Snyder et al., "Introduction to Modern Liquid Chromatography" ($3^{rd}$ ed., John Wiley & Sons, New York, 2009). The theory and practice of MS are described in E. de Hoffmann & V. Stroobant, "Mass Spectroscopy: Principles and Applications" ($3^{rd}$ ed., John Wiley & Sons, New York, 2007).

In one preferred alternative, HPLC is performed employing a reverse phase amide column. A particularly preferred amide column is a 4.6 mm×250 mm column employing amide chemistry in a hydrophilic interaction mode; the column employs ethylene bridged hybrid (BEH) technology. The particles of the column are of spherical shape and have a particle size of 3.5 μm. The particles have a hybrid substrate and have a pore size of 130 Å. A particularly preferred reverse phase amide column is a Waters XBridge BEH amide column No. 186004870 (Waters, Milford Mass.). Other reverse phase amide columns are known in the art.

For the mobile phase, a preferred alternative is to use 100% acetonitrile as Mobile Phase A and 100% water as Mobile Phase B. A preferred flow rate is from about 0.72 mL/min to about 0.88 mL/min; a particularly preferred flow rate is about 0.80 mL min.

A preferred scheme for elution is as follows: (1) 0.00 minutes, 90% of 100% acetonitrile; 10% of 100% water; (2) 3.00 minutes, 90% of 100% acetonitrile; 10% of 100% water; (3) 20.00 minutes, 75% of 100% acetonitrile, 25% of 100% water; (4) 25.00 minutes, 50% of 100% acetonitrile, 50% of 100% water; (5) 30.00 minutes, 50% of 100% acetonitrile, 50% of 100% water; (6) 30.10 minutes, 90% of 100% acetonitrile, 10% of 100% water; and (7) 40.00 minutes, 90% of 100% acetonitrile, 10% of 100% water.

The injection volume can be from about 15 µL to about 35 µL. A preferred injection volume is 25 µL.

The column temperature can be from about 28° C. to about 32° C. A preferred column temperature is about 30° C.

A preferred run time is about 40 minutes. The injector temperature can be at about 5° C. or at about room temperature (about 20° C. to about 22° C.). The analytical method can include a needle wash with 100% acetonitrile.

Typically, in HPLC analytical methods according to the present invention, detection is by means of evaporative light scattering (ELSD). An evaporative light scattering detector (ELSD) atomizes the column eluate, shines light on the resulting particulate components, and detects the resulting scattered light. Theoretically, an ELSD can detect any non-volatile component. The evaporative light scattering detection of a non-chromogenic compound is based on nebulization of the HPLC eluent and evaporation of mobile-phase solvents to produce atomizing solute particles for light scattering detection. This nebulization and solvent evaporation process to produce atomizing analyte solute particles is comparable to the electrospray LC/MS procedure. Typically, the ELSD detection is compatible with electrospray LC/MS.

Implementation of an HPLC method with ELSD detection that is compatible with electrospray LC/MS application typically involves post-column addition of a volatile solvent to enhance evaporation of the aqueous fraction of any mobile phase present. The volatile solvent is typically selected from the group consisting of methanol, ethanol, isopropanol, and acetonitrile.

Typically, the ELSD detection conditions are a temperature from about 36° C. to about 44° C., a gas pressure from about 2.0 bar to about 3.0 bar, and a gain of 7. Preferably, the ELSD conditions are a temperature from about 38° C. to about 42° C., a gas pressure from about 2.25 bar to about 2.75 bar, and a gain of 7. More preferably, the ELSD conditions are a temperature of about 40° C., a gas pressure of about 2.5 bar, and a gain of 7.

Typically, the evaporative light scattering detection is compatible with electrospray LC/MS. Accordingly, in methods according to the present invention, an electrospray tandem mass spectrometer can be installed and connected on-line to an HPLC system with ELSD. Mass spectral data providing molecular information and tandem mass spectral data providing chemical structural information for each of the impurities that may be present in a preparation of dianhydrogalactitol can be collected. Mass spectroscopy in tandem with HPLC will provide molecular ion information and possible chemical structures having a molecular weight consistent with the molecular ion information for each of the observed impurities and degradation products.

In another alternative, preparative HPLC collection of specific DAG-related substance peaks, including impurities present in a preparation of DAG, can be performed.

Accordingly, one analytical method for analyzing the presence and quantity of impurities present in a preparation of dianhydrogalactitol comprises the steps of:

(1) analyzing a preparation of dianhydrogalactitol by subjecting the preparation to high performance liquid chromatography using a reversed phase amide column employing amide chemistry in a hydrophilic interaction mode and ethylene bridged hybrid (BEH) technology with elution with a mobile phase gradient wherein a first mobile phase is 100% acetonitrile and a second mobile phase is 100% water to separate dianhydrogalactitol from dulcitol and other contaminants of the preparation; and (2) determining the relative concentration of one or more peaks resolved by high performance liquid chromatography that represent compounds other than dianhydrogalactitol itself.

The compounds other than dianhydrogalactitol itself can be at least one of: (1) dulcitol; (2) dibromodulcitol; (3) an impurity other than dulcitol; and (4) a degradation product of dianhydrogalactitol.

Suitable conditions for reversed phase chromatographic analysis and ELSD detection are as described above.

In one alternative, a method according to the present invention further comprises the step of analyzing one or more peaks eluting from the high performance liquid chromatography by electrospray tandem mass spectroscopy. In another alternative, a method according to the present invention further comprises the step of preparative HPLC collection of at least one specific dianhydrogalactitol-related substance peak.

If an impurity or degradation product (other than dulcitol) exists, the unknown impurity or degradation product can be identified by separation by column chromatography followed by at least one purification procedure to yield a solid unknown sample which can then be characterized for identification by at least one standard analytical procedure selected from the group consisting of nuclear magnetic resonance (NMR), mass spectroscopy (MS), Fourier transform infrared spectroscopy (FT-IR), elemental analysis, determination of purity by HPLC, and determination of water content by the Karl Fischer titration method. These methods are well known in the art.

In the method as described above, the method can further comprise the step of performing preparative HPLC collection of at least one specific substance peak present in a preparation of dianhydrogalactitol. The at least one specific substance peak present in the preparation of dianhydrogalactitol can be an impurity. Alternatively, the at least one specific substance peak present in the preparation of dianhydrogalactitol can be a degradation product.

The invention is illustrated by the following Example. This Example is for illustrative purposes only, and is not intended to limit the invention.

Example

Reverse Phase HPLC Analysis of Dianhydrogalactitol Preparations Employing Gradient of Acetonitrile and Water In summary, this test procedure is used for determining one or more related substance or substances in a preparation of dianhydrogalactitol (DAG) drug substance and drug product by high performance liquid chromatography (HPLC) with ELSD detection (HPLC-ELSD). A reversed phase column (Waters Amide, 3.5 μm, 4.6×250 mm) with 100% acetonitrile (ACN) as Mobile Phase A and 100% water as Mobile Phase B is used. The flow rate is 0.8 mg/mL. The peak of DAG is detected with a retention time at about 5.20 min. The DAG samples are prepared at target concentration of 8 mg/m L.

Reagents and Reference Standards

Reagents and reference standards include: (1) purified water (H$_2$O), HPLC grade or equivalent; (2) acetonitrile (ACN), HPLC grade or equivalent; and (3) dulcitol reference standard.

Instruments and Apparatus

Instruments and apparatus include: (1) Shimadzu LC20A HPLC system or equivalent equipped with ELSD detector; (2) Waters Amide reverse phase HPLC column, 3.5 μm, 4.6×250 mm, PN: 186004870); (3) Purity water generator; and (4) analytical balance.

Preparation of Solutions

The volumes may be scaled up or down as appropriate for testing. A diluent with acetonitrile/water (85:15, v/v) can be prepared by thoroughly mixing 850 mL of ACN and 150 mL of water. The mobile phases are 100% ACN (Mobile Phase A) and 100% water (Mobile Phase B). Dulcitol linearity standard solutions of 0.016 mg/mL (0.2%), 0.08 mg/mL (1%), and 0.4 mg/mL (5%) are prepared. The weights and volumes given are the recommended amounts for routine quantitative analysis. Alternative amounts may be used, provided that the final concentrations remain the same. The glassware is to be pre-rinsed five times with purified water and ACN to minimize potential contamination.

Other concentrations can be prepared. For example, for a dulcitol concentration standard of 3% (0.24 mg/mL), accurately weigh about 24 mg of dulcitol reference standard into a 100 mL volumetric flask, add 15 mL purified water and sonicate to dissolve, dilute to volume with acetonitrile and mix well. Label them as L-3%-#1 (STD #1) and L-3%-#2 (STD #2). The volumetric flask should be cleaned completely by rinsing with purified water and ACN before use.

One replicate can be prepared for 0.08 mg/mL (1%). For example, accurately weigh about 20 mg of dulcitol reference standard into a 250 mL volumetric flask, add 37.5 mL purified water and sonicate to dissolve, dilute to volume with ACN and mix well. Label it as L-1%.

One replicate can be prepared for 0.016 mg/mL (0.2%). This can be prepared as shown in Table 1.

TABLE 1

| Levels | Example Dilution Procedure | Label AS | Target Concentration (mg/mL) |
|---|---|---|---|
| 0.2% | 2 mL L-1%→ 10 mL | L-0.2% | 0.016 |

The standard solutions can be stored up to 48 hrs at 2-8° C. and can be stored up to 52 hrs at ambient laboratory condition. The standard solutions can be used to generate a standard curve as described further below.

A dulcitol sensitivity solution (0.008 mg/mL (0.1%) in one replicate can be prepared as shown below in Table 2.

TABLE 2

| Levels | Example Dilution Procedure | Label AS | Target Concentration (mg/mL) |
|---|---|---|---|
| 0.1% | 1 mL L-5%-#1→ 50 mL | SS | 0.008 |

A dianhydrogalactitol (DAG) standard solution (8 mg/mL) (for identification purposes only) can be prepared as follows: Accurately weigh, in one replicate, about 80 mg of DAG working standard into clean 10 mL volumetric flasks. Dissolve DAG working standard in approximately 5 mL of diluent, diluted to volume with diluent, and mix. The solution can be liquored and stored frozen for future use until the relevant peaks are no longer detectable in the chromatogram.

The test sample solutions (nominal 8 mg/mL) are prepared as follows. The sample preparation for DAG drug substance or API can be as follows. Accurately weigh, in duplicate, about 80 mg of DAG API sample into clean 10 mL volumetric flasks. Dissolve DAG API sample in approximately 5 mL of diluent, diluted to volume with diluent, and mix. The sample preparation for DAG drug product (lyophilized powder, 40 mg/vial) can be as follows: Clean and remove the closure of the vial. Reconstitute the lyophilized vial with 5.0 mL diluent to yield an 8 mg/mL solution. Prepare samples in duplicate (using 2 vials). The sample solutions can be stored up to 48 hrs at 2-8° C. and 52 hrs at ambient laboratory conditions.

Chromatographic Conditions

Chromatographic conditions are shown in Table 3.

TABLE 3

| Mobile Phase | Mobile phase A: 100% ACN |
| | Mobile phase B: 100% Water |
| Column | Waters Amide 4.6 * 250 mm, 3.5 μm |

| | Time (min) | Flow Rate (mL/min) | MPA % | MPB % |
|---|---|---|---|---|
| Gradient | 0.00 | 0.8 | 90 | 10 |
| | 3.00 | 0.8 | 90 | 10 |
| | 20.00 | 0.8 | 75 | 25 |
| | 25.00 | 0.8 | 50 | 50 |
| | 30.00 | 0.8 | 50 | 50 |
| | 30.10 | 0.8 | 90 | 10 |
| | 40.00 | 0.8 | 90 | 10 |

| ELSD Conditions | Temperature: 40° C. |
| | Gas pressure 2.5 bar |
| | Gain: 7 |
| Injection Volume | 25 μL |
| Column Temperature | 30° C. |
| Run Time | 40 min |
| Injector Temperature | RT or 5° C. |
| Needle Wash | 100% ACN |

The HPLC column is to be conditioned at initial method conditions and equilibrated prior to the analysis of samples.

Injection Sequence

After ensuring that the system suitability requirements stated below are satisfied, sample analysis can be performed. The injection sequence is shown in Table 4.

TABLE 4

| Ser. No. | Sample Name | No. of Injection |
|---|---|---|
| 1 | Blank (Diluent) | 1 or more |
| 2 | Sensitivity Solution (SS) | 1 |
| 3 | L-0.2% | 1 |
| 4 | L-1% | 1 |
| 5 | STD#1 (L-3%#1) | 5 |

TABLE 4-continued

| Ser. No. | Sample Name | No. of Injection |
|---|---|---|
| 6 | STD#2 (L-3%#2) | 1 |
| 7 | DAG standard solution (only for identification purpose) | 1 |
| 8 | Sample Solutions | 1 of each |
| 9 | STD#1 (L-3%#1) | 1 |

The sequence is bracketed by injecting STD #1 (L-3%#1) once, followed by no more than 6 injections of sample solution and, at the end of the sequence, again injecting STD #1 (L-3%#1).

System Suitability

For the blank, ensure that the system is clean and stable and there is no interference peak observed in the blank chromatograms at the retention time of dulcitol. If any interference, the interference should be not more than the dulcitol peak in the sensitivity solution.

For the sensitivity solution, the signal to noise (S/N) of dulcitol peak in the sensitivity solution should be no less than 10.

For correlation (r), the correlation of the logarithmic calibration curve for L-0.2%, L-1% and L-3%#1 (first injection) should be no less than 0.980.

For the standard solution, the relative standard deviation (RSD) of Lg (peak area) of dulcitol for the first five initial injections of STD #1 (L-3%#1) should be 5%. The tailing factor of dulcitol peak in the first injection of STD #1 (L-3%#1) should be 2.0. The recovery of STD #2 (L-3%#2) should be within 95%-105%. The recovery of standard solution #2 is calculated according to Equation (1):

$$\text{Check standard recovery} = \frac{lg(C_{STD\#1})}{lg(C_{STD\#2})} \times \frac{lg(A_{STD\#2})}{lg(A_{STD\#1})} \times 100\%, \quad \text{(Equation (1))}$$

wherein: $C_{STD\ \#1}$ is the concentration of dulcitol reference standard in standard solution #1 (STD #1) (mg/mL); $C_{STD\ \#2}$ is the concentration of dulcitol reference standard in standard solution #2 (STD #2) (mg/mL); $A_{STD\ \#1}$ is the average peak area of dulcitol in five initial injections of standard solution #1 (STD #1); and $A_{STD\ \#2}$ is the average peak area of dulcitol in five initial injections of standard solution #2 (STD #2).

For bracketing the standard solution, the ratio between the Lg(peak area) of bracketing injection and the average Lg(peak area) of first five injections of STD #1 (L-3%#1) should be within 95%-105%.

Figure 2:
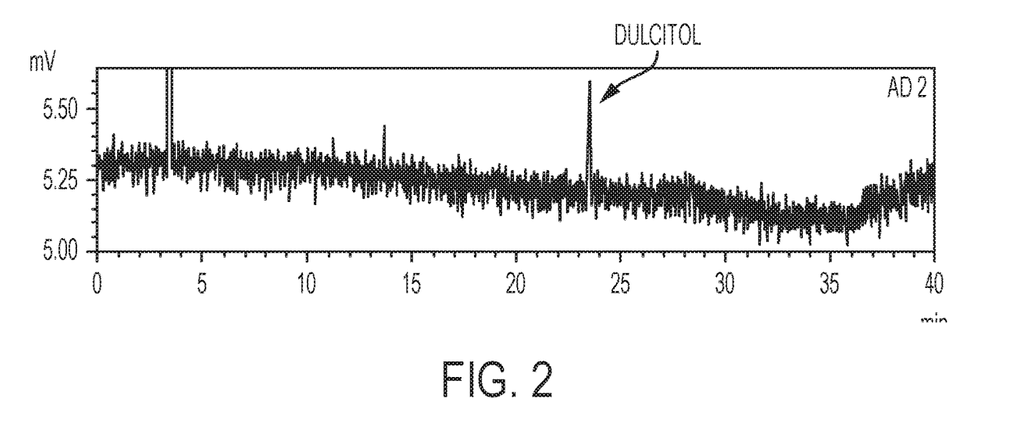
FIG. 2 is a graph showing the results of chromatography of an 0.004 mg/mL dulcitol solution (0.05% of the nominal concentration) to determine the detection limit (LOD) for dulcitol.

For the detection limit (LOD), the signal to noise (S/N) should be no less than 3. The determination of the detection limit (LOD) for dulcitol, one of the expected impurities in a preparation of dianhydrogalactitol, is shown in FIG. 2. FIG. 2 is a graph showing the results of chromatography of an 0.004 mg/mL dulcitol solution (0.05% of the nominal concentration) to determine the detection limit (LOD) for dulcitol.

Figure 3:
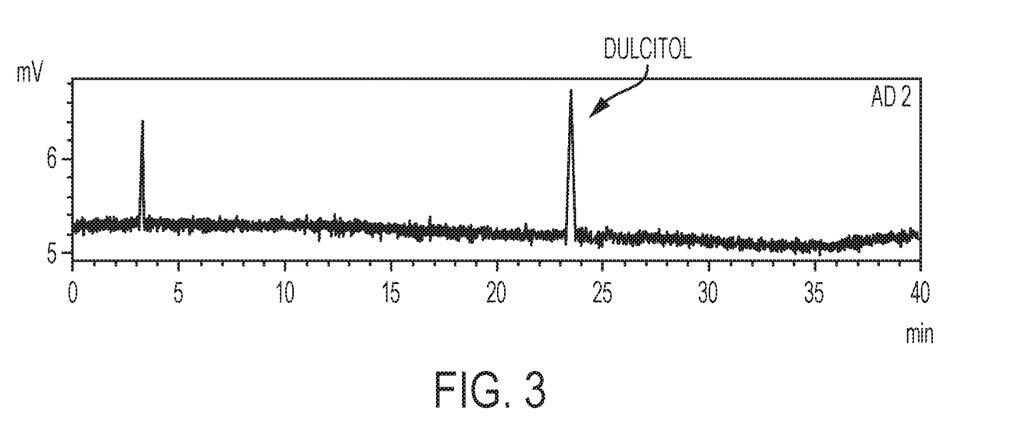
FIG. 3 is a graph showing the results of chromatography of an 0.008 mg/mL dulcitol solution (0.1% of the nominal concentration) to determine the quantitation limit (LOQ) for dulcitol.

For the quantitation limit (LOQ), the signal to noise (S/N) should be no less than 10. The determination of the quantitation limit (LOQ) for dulcitol is shown in FIG. 3. FIG. 3 is a graph showing the results of chromatography of an 0.008 mg/mL dulcitol solution (0.1% of the nominal concentration) to determine the quantitation limit (LOQ) for dulcitol.

The mean recovery (n=3) for each level should be within about 80% to about 120%.

For repeatability, for 0.1% to 0.4% levels, the RSD % should be recorded. For 0.5% and above, the RSD % should be ≤20%. The combined RSD % should be 20%.

For variability of results with respect to the ELSD gas pressure, the absolute difference should be no more than 0.2% for an impurity at ≤1.0%. For an impurity >1.0%, the relative difference should be controlled within ±20%. No new impurities ≥0.1% should be observed.

With respect to solution stability, the recovery of the aged solutions should be within 85%-115% of the initial assay. The absolute difference should be no more than 0.2% for an impurity at ≤1.0%. For an impurity >1.0%, the result of the aged solution should be within 80%-120% of the original. No new impurities at ≥1.0% should be observed.

Identification

For placebo, no chromatographic peak more than the dulcitol peak in the Sensitivity Solution (SS) can be detected corresponding to the DAG peak in the DAG standard chromatogram. For DAG active substance, the retention time for DAG in the sample and DAG standard are essentially the same (within ±5%).

Calculation

Figure 4:
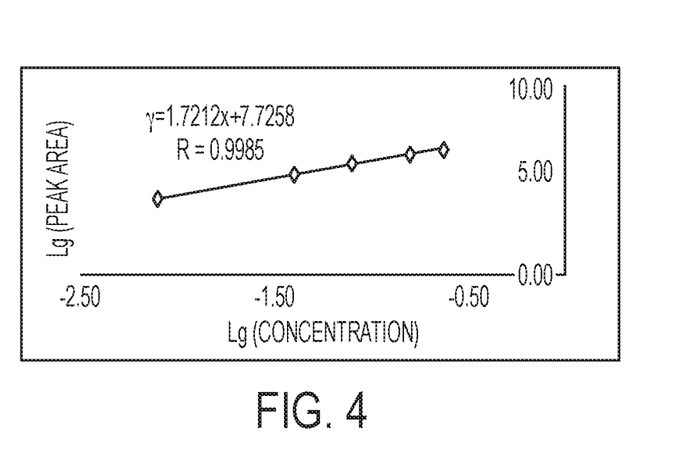
FIG. 4 is a graph showing the results of a linearity test using dulcitol.

For individual related substances, the calculation curve of dulcitol using linearity working standards is performed as follows (Equation (2):

$$lg\ A_{STD} = b + k \times lg\left(\frac{W_{STD} \times P}{V_{STD}}\right), \quad \text{(Equation (2))}$$

where: $A_{STD}$ is represents the area of dulcitol for Linearity Standard Solution (for L-3%, the first injections of STD #1 can be used); $V_{STD}$ is the dilution volume for Linearity Standard Solution (mL); $W_{STD}$ is the dulcitol weight of Linearity Standard Solution (mg); P is the purity (or content) of dulcitol; b is the Y-intercept of the established calibration curve; and k is the slope of the established calibration curve. The percentage of the individual related substance is calculated by Equation (3)

$$\text{Individual Related Substance \%} = \frac{10^{(lgA_{SPL}-b)/k} \times V_{SPL}}{LC\ \text{or}\ W_{SPL}} \times 100, \quad \text{(Equation (3))}$$

where: $A_{SPL}$ is the area of individual related substance; $V_{SPL}$ is the dilution volume of sample solution; b is the Y-intercept of the established calibration curve; k is the slope of the established calibration curve; LC is the label claim (the nominal quantity as stated on the label) of DAG in each vial (LC=40 mg for Drug Product); and $W_{SPL}$ is the DAG drug substance weight (mg). The results of a linearity test using dulcitol are shown in FIG. 4; these results are from Table 18, below.

For the total related substance, the calculation for total related substances should sum all individual related substances not less than 0.1%. Void and blank peaks should not be added to the total related substances.

Reporting

For reporting of individual related substances, for all impurities that not less than 0.1%, report all impurities that not less than 0.1% referenced to their relative retention time (RRT) or name, and present to two decimal places. If two testing results are not less than specification limit (0.1%), the average result should be reported as the final result. But if one testing result is less than 0.1%, the maximal result should be reported as the final result. For total related substances (total impurities), sum all individual impurities that are no less than 0.1%. Report the total related substance to two decimal places.

References

Reference standards are shown in Table 5.

TABLE 5

| Composition | Unit Formula | |
|---|---|---|
| | Qty (mg)/Vial | w/w, % |
| DAG for Injection | 40 | 100 |
| Total | 40 | 100 |

Results

All system suitability criteria were met. There were no noticeable interference peaks observed at the retention time of the DAG peak, DBD, and dulcitol in the diluent chromatogram. The difference of the retention time of DAG peaks in the sample and standard solutions ranged from 0% to 3%. The signal to noise (S/N) with respect to the detection limit was 6, 6, and 3 in triplicate replications. The signal to noise (S/N) with respect to the quantitation limit was 22, 20, and 16 in triplicate replications. The correlation coefficient (r) was 0.9985 with a slope of 1.7212 and a y-intercept of 7.7258. The mean recovery for levels of 0.5%, 1.0%, and 3.0% is shown in Table 6, below. The RSD % are shown in Tables 7 (Run 1) and Table 8 (Run 2), below, for two duplicate runs. For P-0.5% (contaminants present at the 0.5% level or higher), dulcitol is shown in Table 9, below; in Table 9, dulcitol was shown to be present at a level of 0.59%. The combined RSD % for intermediate precision (a measure of precision under a defined set of conditions: same measurement procedure, same measuring system, same location, and replicate measurements on the same or similar objects over an extended period of time) for the level of 0.5% is shown in Table 10, below. The absolute differences for ELSD gas pressures of 2.6 bar and 2.4 bar are shown in Table 11, below. No impurity at >1.0% was observed, and no new impurity at ≤0.1% was observed. Results for ELSD temperature of 39° C. and 41° C. are shown in Table 12, below. No impurity at >1.0% was observed, and no new impurity at ≤0.1% was observed.

Solution Stability

The experimental approach for determining solution stability was as follows: For a standard solution, a dulcitol standard solution was prepared at 1.0% of DAG nominal conc. in one replicate and placed the solution under ambient laboratory conditions and refrigerated conditions (2-8° C.), respectively, using 1% Linearity standard solutions). The solution was reanalyzed at different time intervals, such as 2 hours, 4 hours, 8 hours, 24 hours and 48 hours. For time points of less than 24 hours, solution stability is evaluated against fresh standards. The recovery of the aged solutions is evaluated. For sample solutions, a sample solution at a specified DAG nominal concentration was prepared in one replicate and placed under laboratory conditions at ambient temperature or under refrigerated conditions (2-8° C.). The solution was reanalyzed at different time intervals, such as 2 hours, 4 hours, 8 hours, 24 hours and 48 hours. For time points of less than 24 hours, solution stability is evaluated against fresh standards.

Results for variability with respect to aging at 2-8° C. and at ambient laboratory conditions are shown in Table 13, below. For impurities, with respect to aging at ambient laboratory conditions, results are shown in Table 14, below. No new impurities at ≥0.1% were observed. For impurities, with respect to aging at 2-8° C., results are shown in Table 15, below. No new impurities at ≥0.1% were observed.

TABLE 6

| Level | Avg. Recovery(%) | RSD % (n = 3) |
|---|---|---|
| 0.5% | 120 | 2.1 |
| 1.0% | 116 | 0.9 |
| 3.0% | 95 | 0.1 |

TABLE 7

| Run 1: | | |
|---|---|---|
| Peak Name | Avg. Content (%) | RSD (n = 6) |
| RRT 0.48 | 0.18 | 2.9 |
| RRT 0.51 | 0.34 | 1.1 |
| RRT 0.56 | 0.28 | 1.0 |
| RRT 0.71 | 1.06 | 0.7 |
| Dulcitol | 0.15 | 2.9 |
| RRT 1.02 | 0.08 | 5.2 |
| RRT 1.07 | 0.08 | 4.0 |

TABLE 8

| Run 2: | | |
|---|---|---|
| Peak Name | Avg. Content (%) | RSD (n = 6) |
| RRT 0.48 | 0.23 | 1.5 |
| RRT 0.56 | 0.35 | 1.8 |
| RRT 0.71 | 0.67 | 0.8 |
| Dulcitol | 0.20 | 1.8 |
| RRT 1.07 | 0.21 | 3.8 |
| RRT 1.19 | 0.15 | 2.8 |
| RRT 1.27 | 0.12 | 10.1 |

TABLE 9

| P-0.5% | | |
|---|---|---|
| Peak Name | Avg. Content (%) | RSD (n = 6) |
| Dulcitol | 0.59 | 0.9 |

TABLE 10

| Level | RSD % (n = 12) |
|---|---|
| 0.5% | 2.1 |

TABLE 11

| Peak Name | Absolute difference (%) |
|---|---|
| 2.6 bar: | |
| RRT 0.48 | 0.001 |
| RRT 0.51 | 0.01 |
| RRT 0.56 | 0.01 |
| RRT 0.71 | 0.02 |
| Dulcitol | 0.004 |

TABLE 11-continued

| Peak Name | Absolute difference (%) |
|---|---|
| 2.4 bar: | |
| RRT 0.48 | 0.01 |
| RRT 0.51 | 0.01 |
| RRT 0.56 | 0.01 |
| RRT 0.71 | 0.02 |
| Dulcitol | 0.001 |

TABLE 12

| Peak Name | Absolute Difference (%) |
|---|---|
| 39° C.: | |
| RRT 0.48 | 0.01 |
| RRT 0.51 | 0.01 |
| RRT 0.56 | 0.003 |
| RRT 0.71 | 0.04 |
| Dulcitol | 0.02 |
| RRT 1.02 | 0.01 |
| RRT 1.07 | 0.01 |
| 41° C.: | |
| RRT 0.48 | 0.001 |
| RRT 0.51 | 0.0001 |
| RRT 0.56 | 0.01 |

TABLE 12-continued

| Peak Name | Absolute Difference (%) |
|---|---|
| RRT 0.71 | 0.01 |
| Dulcitol | 0.002 |
| RRT 1.02 | 0.001 |
| RRT 1.07 | 0.01 |

TABLE 13

| Time point (hrs) | Recovery (v.s. Initial, %) |
|---|---|
| Ambient Laboratory Conditions: | |
| 0 | N/A |
| 2 | 100 |
| 4 | 99 |
| 8 | 99 |
| 27 | 101 |
| 52 | 99 |
| 2-8° C.: | |
| 0 | N/A |
| 2 | 100 |
| 4 | 100 |
| 8 | 99 |
| 25 | 100 |
| 48 | 100 |

TABLE 14

| | Ambient Laboratory Conditions | | | | | | | | | | |
|---|---|---|---|---|---|---|---|---|---|---|---|
| Sample | Content(%) | | | | | | Absolute difference (%) | | | | |
| Name | 0 h | 2 h | 4 h | 8 h | 25 h | 48 h | 2 h | 4 h | 8 h | 25 h | 48 h |
| RRT 0.48 | 0.15 | 0.16 | 0.15 | 0.16 | 0.18 | 0.17 | 0.01 | 0.004 | 0.01 | 0.03 | 0.02 |
| RRT 0.51 | 0.32 | 0.32 | 0.32 | 0.31 | 0.33 | 0.33 | 0.002 | 0.01 | 0.01 | 0.01 | 0.01 |
| RRT 0.56 | 0.37 | 0.36 | 0.36 | 0.36 | 0.38 | 0.38 | 0.01 | 0.004 | 0.01 | 0.02 | 0.01 |
| Dulcitol | 0.19 | 0.19 | 0.20 | 0.19 | 0.21 | 0.20 | 0.001 | 0.01 | 0.003 | 0.02 | 0.01 |
| RRT 1.02 | 0.12 | 0.11 | 0.12 | 0.11 | 0.13 | 0.12 | 0.004 | 0.01 | 0.01 | 0.01 | 0.01 |
| RRT 1.07 | 0.15 | 0.14 | 0.13 | 0.13 | 0.16 | 0.14 | 0.01 | 0.02 | 0.02 | 0.01 | 0.01 |
| RRT 1.19 | 0.11 | 0.10 | 0.10 | 0.10 | 0.11 | 0.09 | 0.002 | 0.01 | 0.004 | 0.01 | 0.01 |
| RRT 1.27 | 0.08 | 0.09 | 0.07 | 0.08 | 0.08 | 0.08 | 0.004 | 0.01 | 0.002 | 0.002 | 0.004 |
| Sample | Content(%) | | | | | | Percent Vs. Initial (%) | | | | |
| Name | 0 h | 2 h | 4 h | 8 h | 25 h | 48 h | 2 h | 4 h | 8 h | 25 h | 48 h |
| RRT 0.71 | 1.24 | 1.24 | 1.22 | 1.22 | 1.24 | 1.21 | 100 | 98 | 98 | 100 | 98 |

TABLE 15

| | 2-8° C. | | | | | | | | | | |
|---|---|---|---|---|---|---|---|---|---|---|---|
| Sample | Content(%) | | | | | | Absolute difference (%) | | | | |
| Name | 0 h | 2 h | 4 h | 8 h | 27 h | 52 h | 2 h | 4 h | 8 h | 27 h | 52 h |
| RRT 0.48 | 0.15 | 0.16 | 0.17 | 0.18 | 0.25 | 0.29 | 0.002 | 0.01 | 0.02 | 0.1 | 0.1 |
| RRT 0.51 | 0.32 | 0.31 | 0.32 | 0.32 | 0.34 | 0.32 | 0.01 | 0.001 | 0.002 | 0.02 | 0.005 |
| RRT 0.56 | 0.36 | 0.35 | 0.37 | 0.36 | 0.37 | 0.36 | 0.01 | 0.01 | 0.0004 | 0.01 | 0.001 |
| Dulcitol | 0.23 | 0.24 | 0.24 | 0.25 | 0.25 | 0.24 | 0.004 | 0.01 | 0.01 | 0.02 | 0.01 |
| RRT 1.02 | 0.11 | 0.12 | 0.12 | 0.12 | 0.13 | 0.13 | 0.01 | 0.01 | 0.003 | 0.02 | 0.01 |
| RRT 1.07 | 0.15 | 0.14 | 0.14 | 0.15 | 0.18 | 0.15 | 0.002 | 0.01 | 0.0005 | 0.03 | 0.001 |
| RRT 1.19 | 0.10 | 0.09 | 0.09 | 0.09 | 0.10 | 0.10 | 0.01 | 0.01 | 0.01 | 0.001 | 0.01 |
| RRT 1.22~1.23 | 0.08 | 0.09 | 0.08 | 0.07 | 0.09 | 0.08 | 0.01 | 0.003 | 0.01 | 0.01 | 0.0004 |
| RRT 1.27 | 0.10 | 0.10 | 0.09 | 0.10 | 0.10 | 0.09 | 0.002 | 0.01 | 0.0003 | 0.003 | 0.01 |

TABLE 15-continued

| | 2-8° C. | | | | | | | | | |
|---|---|---|---|---|---|---|---|---|---|---|
| Sample | Content(%) | | | | | | Percent Vs. Initial (%) | | | |
| Name | 0 h | 2 h | 4 h | 8 h | 27 h | 52 h | 2 h | 4 h | 8 h | 27 h | 52 h |
| RRT 0.71 | 1.10 | 1.13 | 1.11 | 1.12 | 1.13 | 1.12 | 103 | 101 | 102 | 103 | 102 |

Further details on system suitability are shown in Tables 16 and 17, below, showing that criteria for consistency of recovery are met.

TABLE 16

| Run No. | Blank | S/N | Correl (r) | RSD | Tailing Factor | Standard Recovery | Bracket Recovery |
|---|---|---|---|---|---|---|---|
| Run 1 | Meet | 23 | 0.9959 | 0.3% | Meet | 99% | 99%, 98%, 98%, 97%, 96%, 96%, 96%, 96%, 96%, 96%, |
| Run 2 | Meet | 19 | 0.9974 | 0.02% | Meet | 100% | 100% |
| Run 3 | Meet | 14 | 0.9975 | 0.1% | Meet | 98% | 100% |
| Run 4 | Meet | 12 | 0.9973 | 0.01% | Meet | 97% | 100% |
| Run 5 | Meet | 14 | 0.9975 | 0.1% | Meet | 101% | 100% |
| Run 6 | Meet | 13 | 0.9939 | 0.2% | Meet | 99% | 100% |
| Run 7 | Meet | 13 | 0.9948 | 0.5% | Meet | 98% | 99% |

TABLE 17

| Run No. | Blank | S/N | Correl (r) | RSD | Tailing Factor | Standard Recovery | Bracket Recovery |
|---|---|---|---|---|---|---|---|
| Run 8 | Meet | 14 | 0.9983 | 0.02% | Meet | 100% | 100%, 100%, 100%, 100%, 100% |
| Run 9 | Meet | 10 | 0.9981 | 0.1% | Meet | 100% | 100%, 100%, 100%, 100% |
| Run 10 | Meet | 13 | 0.9988 | 0.1% | Meet | 100% | 100%, 100%, 100%, 100% |

Figure 1:
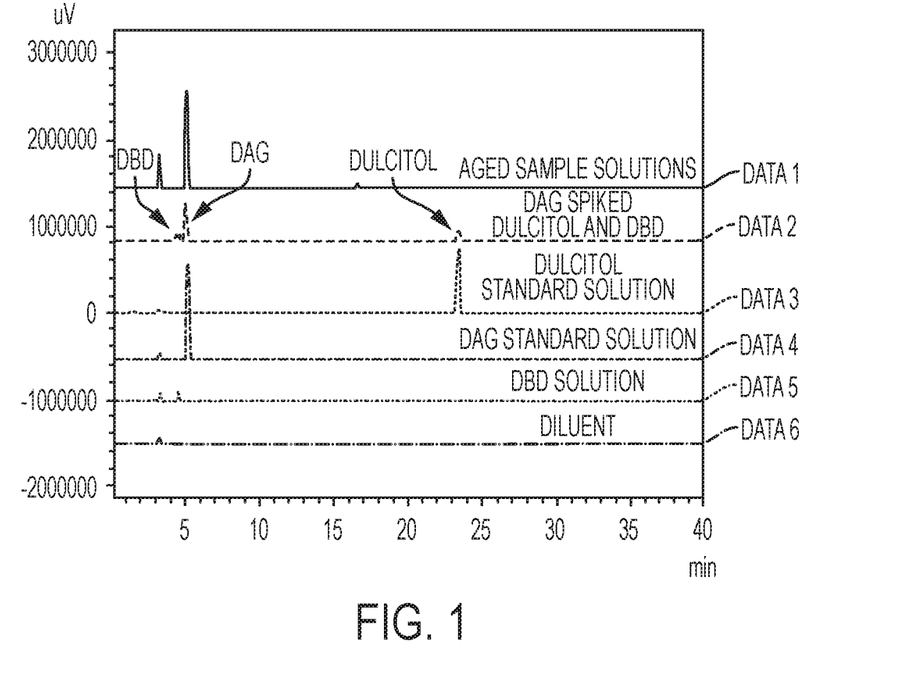
FIG. 1 is a graph showing overlaid chromatograms of blank, a fresh tablet sample, a standard solution, and a mock sample solution (DAG is dianhydrogalactitol and DBD is dibromodulcitol).

FIG. 1 is a graph showing overlaid chromatograms of blank, a fresh tablet sample, a standard solution, and a mock sample solution (DAG is dianhydrogalactitol and DBD is dibromodulcitol). In FIG. 1, there are no noticeable interference peaks observed at the retention times of the DAG peak, DBD and dulcitol, so the resolution of these substances is clearly established. The retention times of the DAG peak in the sample and standard solution are within ±5%.

Figure 5:
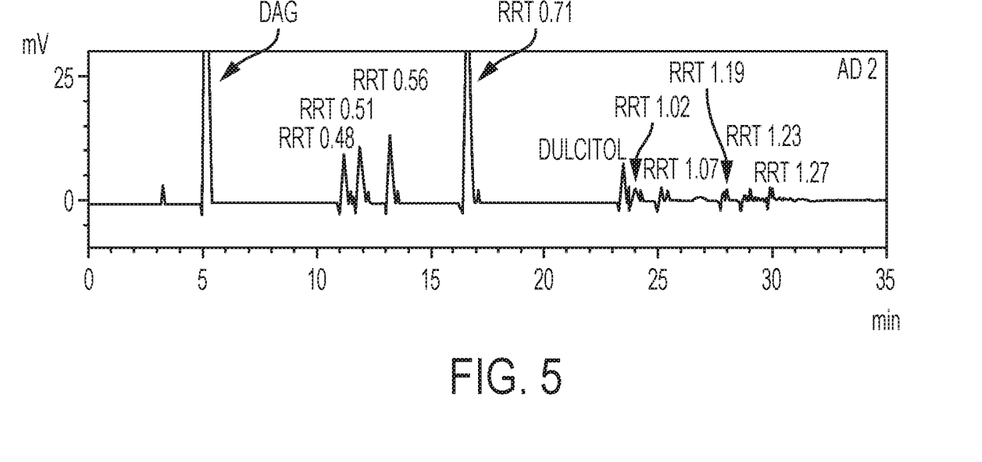
FIG. 5 is a graph showing impurities in a sample solution.

FIG. 5 is a graph showing impurities in a sample solution. The impurities, besides dulcitol, include impurities at relative retention times (RRTs) of 0.48, 0.51, 0.56, 0.71, 1.02, 1.07, 1.19, 1.23, and 1.27.

Table 18, below, shows the linearity results for dulcitol.

TABLE 18

| Level | Actual Conc. (mg/mL) | lg (Actual Conc.) | Peak Area | lg (Peak Area) | Slope | Y-intercept | Correl (r) |
|---|---|---|---|---|---|---|---|
| 0.1% | 0.00797 | −2.0985 | 11663 | 4.0668 | 1.7212 | 7.7258 | 0.9985 |
| 0.5% | 0.03985 | −1.3996 | 236370 | 5.3736 | | | |
| 1.0% | 0.07970 | −1.0985 | 774592 | 5.8891 | | | |
| 2.0% | 0.15940 | −0.7975 | 2238583 | 6.3500 | | | |
| 3.0% | 0.23910 | −0.6214 | 3939708 | 6.5955 | | | |

Table 19, below, shows the accuracy results for dulcitol.

TABLE 19

| Level | Replicate | Peak Area | Recovery % | Avg. Rec. % (n = 3) | RSD % (n = 3) |
|---|---|---|---|---|---|
| Control | 1 | 0 | | N/A | |
| | 2 | 0 | | | |
| | 3 | 0 | | | |
| 0.5% | 1 | 253384 | 117.95 | 120 | 2.1 |
| | 2 | 254422 | 118.22 | | |
| | 3 | 270620 | 122.46 | | |
| 1.0% | 1 | 839048 | 116.78 | 116 | 0.9 |
| | 2 | 829611 | 116.03 | | |
| | 3 | 812409 | 114.65 | | |
| 3.0% | 1 | 4021051 | 95.18 | 95 | 0.1 |
| | 2 | 4003232 | 94.94 | | |
| | 3 | 4004851 | 94.96 | | |

Table 20, below, shows the precision (repeatability) results for Run 1.

TABLE 20

| Peak Name | Content (%, #1) | Content (%, #2) | Content (%, #3) | Content (%, #4) | Content (%, #5) | Content (%, #6) | Avg. Content (%) | RSD % (n = 6) |
|---|---|---|---|---|---|---|---|---|
| RRT 0.48 | 0.17 | 0.17 | 0.17 | 0.18 | 0.18 | 0.18 | 0.18 | 2.9 |
| RRT 0.51 | 0.33 | 0.34 | 0.33 | 0.34 | 0.34 | 0.34 | 0.34 | 1.1 |
| RRT 0.56 | 0.27 | 0.28 | 0.27 | 0.28 | 0.28 | 0.28 | 0.28 | 1.0 |
| RRT 0.71 | 1.06 | 1.07 | 1.07 | 1.05 | 1.07 | 1.06 | 1.06 | 0.7 |
| Dulcitol | 0.15 | 0.16 | 0.15 | 0.16 | 0.15 | 0.15 | 0.15 | 2.9 |
| RRT 1.02 | 0.09 | 0.08 | 0.09 | 0.08 | 0.08 | 0.08 | 0.08 | 5.2 |
| RRT 1.07 | 0.08 | 0.08 | 0.09 | 0.08 | 0.08 | 0.08 | 0.08 | 4.0 |

Table 21, below, shows the precision (repeatability) results for Run 2.

TABLE 21

| Peak Name | Content (%, #1) | Content (%, #2) | Content (%, #3) | Content (%, #4) | Content (%, #5) | Content (%, #6) | Avg. Content (%) | RSD % (n = 6) |
|---|---|---|---|---|---|---|---|---|
| RRT 0.48 | 0.22 | 0.23 | 0.22 | 0.23 | 0.23 | 0.23 | 0.23 | 1.5 |
| RRT 0.56 | 0.35 | 0.34 | 0.34 | 0.34 | 0.35 | 0.35 | 0.35 | 1.8 |
| RRT 0.71 | 0.67 | 0.68 | 0.67 | 0.68 | 0.67 | 0.67 | 0.67 | 0.8 |
| Dulcitol | 0.20 | 0.20 | 0.21 | 0.20 | 0.20 | 0.20 | 0.20 | 1.8 |
| RRT 1.07 | 0.21 | 0.21 | 0.21 | 0.21 | 0.21 | 0.19 | 0.21 | 3.8 |
| RRT 1.19 | 0.14 | 0.15 | 0.15 | 0.15 | 0.15 | 0.16 | 0.15 | 2.8 |
| RRT 1.27 | 0.12 | 0.14 | 0.12 | 0.11 | 0.14 | 0.11 | 0.12 | 10.1 |

Table 22, below, shows the precision (repeatability) results at P-0.5%.

TABLE 22

| Peak Name | Content(%) | Avg. Content(%) | RSD of Content (% n = 6) |
|---|---|---|---|
| Dulcitol | 0.5796 | 0.59 | 0.9 |
| | 0.5789 | | |
| | 0.5878 | | |
| | 0.5930 | | |
| | 0.5890 | | |
| | 0.5859 | | |

Table 23, below, shows the precision results (intermediate precision) for dulcitol.

TABLE 23

| Analyst | Content(%) | Avg. Content (%, n = 12) | RSD of Content (%, n = 12) |
|---|---|---|---|
| 1st | 0.5796 | 0.58 | 2.1 |
|  | 0.5789 |  |  |
|  | 0.5878 |  |  |
|  | 0.5930 |  |  |
|  | 0.5890 |  |  |
|  | 0.5859 |  |  |
| 2nd | 0.5683 |  |  |
|  | 0.5570 |  |  |
|  | 0.5716 |  |  |
|  | 0.5682 |  |  |
|  | 0.5618 |  |  |
|  | 0.5597 |  |  |

Table 24, below, shows the results of a study with variation of ELSD temperature.

TABLE 24

| Sample Name | Content % 40° C. | Content % 39° C. | Content % 41° C. | Absolute Difference between 39° C. and 40° C. | Absolute Difference between 41° C. and 40° C. |
|---|---|---|---|---|---|
| RRT 0.48 | 0.1787 | 0.1704 | 0.1795 | 0.01 | 0.001 |
| RRT 0.51 | 0.3164 | 0.3113 | 0.3163 | 0.01 | 0.0001 |
| RRT 0.56 | 0.3021 | 0.2992 | 0.3096 | 0.003 | 0.01 |
| RRT 0.71 | 0.8608 | 0.8961 | 0.8724 | 0.04 | 0.01 |
| Dulcitol | 0.1814 | 0.1660 | 0.1789 | 0.02 | 0.002 |
| RRT 1.02 | 0.1037 | 0.0932 | 0.1044 | 0.01 | 0.001 |
| RRT 1.07 | 0.1094 | 0.1005 | 0.1197 | 0.01 | 0.01 |

Table 25, below, shows the results of a study with variation of ELSD gas pressure.

TABLE 25

| Sample Name | Content % 2.5bar | Content % 2.6bar | Content % 2.4bar | Absolute Difference between 2.6bar and 2.5bar | Absolute Difference between 2.4bar and 2.5bar |
|---|---|---|---|---|---|
| RRT 0.48 | 0.2041 | 0.2051 | 0.2092 | 0.001 | 0.01 |
| RRT 0.51 | 0.2511 | 0.2616 | 0.2651 | 0.01 | 0.01 |
| RRT 0.56 | 0.2626 | 0.2687 | 0.2694 | 0.01 | 0.01 |
| RRT 0.71 | 0.8570 | 0.8730 | 0.8771 | 0.02 | 0.02 |
| Dulcitol | 0.1591 | 0.1631 | 0.1578 | 0.004 | 0.001 |

Table 26, below, shows the results of standard solution stability at 2-8° C. for Run 1.

TABLE 26

| Time point | Concentration (mg/mL) | Assay(%) | Recovery (v.s. Initial, %) |
|---|---|---|---|
| 0 h | 0.0895 | 109.233 | N/A |
| 2 h | 0.0894 | 109.076 | 100 |
| 4 h | 0.0895 | 109.164 | 100 |
| 8 h | 0.0888 | 108.302 | 99 |
| 25 h | 0.0894 | 109.056 | 100 |
| 48 h | 0.0893 | 108.947 | 100 |

Table 27, below, shows the results of standard solution stability at 2-8° C. for Run 2.

TABLE 27

| Sample Name | Content(%) | | | | | | Absolute difference (%) | | | | |
|---|---|---|---|---|---|---|---|---|---|---|---|
| | 0 h | 2 h | 4 h | 8 h | 25 h | 48 h | 2 h | 4 h | 8 h | 25 h | 48 h |
| RRT 0.48 | 0.15 | 0.16 | 0.15 | 0.16 | 0.18 | 0.17 | 0.01 | 0.004 | 0.01 | 0.03 | 0.02 |
| RRT 0.51 | 0.32 | 0.32 | 0.32 | 0.31 | 0.33 | 0.33 | 0.002 | 0.01 | 0.01 | 0.01 | 0.01 |
| RRT 0.56 | 0.37 | 0.36 | 0.36 | 0.36 | 0.38 | 0.38 | 0.01 | 0.004 | 0.01 | 0.02 | 0.01 |
| Dulcitol | 0.19 | 0.19 | 0.20 | 0.19 | 0.21 | 0.20 | 0.001 | 0.01 | 0.003 | 0.02 | 0.01 |
| RRT 1.02 | 0.12 | 0.11 | 0.12 | 0.11 | 0.13 | 0.12 | 0.004 | 0.01 | 0.01 | 0.01 | 0.01 |
| RRT 1.07 | 0.15 | 0.14 | 0.13 | 0.13 | 0.16 | 0.14 | 0.01 | 0.02 | 0.02 | 0.01 | 0.01 |
| RRT 1.19 | 0.11 | 0.10 | 0.10 | 0.10 | 0.11 | 0.09 | 0.002 | 0.01 | 0.004 | 0.01 | 0.01 |
| RRT 1.27 | 0.08 | 0.09 | 0.07 | 0.08 | 0.08 | 0.08 | 0.004 | 0.01 | 0.002 | 0.002 | 0.004 |

| Sample Name | Content(%) | | | | | | Percent Vs. Initial (%) | | | | |
|---|---|---|---|---|---|---|---|---|---|---|---|
| | 0 h | 2 h | 4 h | 8 h | 25 h | 48 h | 2 h | 4 h | 8 h | 25 h | 48 h |
| RRT 0.71 | 1.24 | 1.24 | 1.22 | 1.22 | 1.24 | 1.21 | 100 | 98 | 98 | 100 | 98 |

Table 28, below, shows the results of standard solution stability at ambient laboratory conditions for Run 1.

TABLE 28

| Time point | Concentration (mg/mL) | Assay(%) | Recovery (v.s. Initial, %) |
|---|---|---|---|
| 0 h | 0.0898 | 109.944 | N/A |
| 2 h | 0.0897 | 109.778 | 100 |
| 4 h | 0.0891 | 109.059 | 99 |
| 8 h | 0.0887 | 108.590 | 99 |
| 25 h | 0.0903 | 110.553 | 101 |
| 48 h | 0.0891 | 108.986 | 99 |

Table 29, below, shows the results of standard solution stability at ambient laboratory conditions for Run 2.

TABLE 29

| Sample Name | Content(%) | | | | | | Absolute difference (%) | | | | |
|---|---|---|---|---|---|---|---|---|---|---|---|
| | 0 h | 2 h | 4 h | 8 h | 27 h | 52 h | 2 h | 4 h | 8 h | 27 h | 52 h |
| RRT 0.48 | 0.15 | 0.16 | 0.17 | 0.18 | 0.25 | 0.29 | 0.002 | 0.01 | 0.02 | 0.1 | 0.1 |
| RRT 0.51 | 0.32 | 0.31 | 0.32 | 0.32 | 0.34 | 0.32 | 0.01 | 0.001 | 0.002 | 0.02 | 0.005 |
| RRT 0.56 | 0.36 | 0.35 | 0.37 | 0.36 | 0.37 | 0.36 | 0.01 | 0.01 | 0.0004 | 0.01 | 0.001 |
| Dulcitol | 0.23 | 0.24 | 0.24 | 0.25 | 0.25 | 0.24 | 0.004 | 0.01 | 0.01 | 0.02 | 0.01 |
| RRT 1.02 | 0.11 | 0.12 | 0.12 | 0.12 | 0.13 | 0.13 | 0.01 | 0.01 | 0.003 | 0.02 | 0.01 |
| RRT 1.07 | 0.15 | 0.14 | 0.14 | 0.15 | 0.18 | 0.15 | 0.002 | 0.01 | 0.0005 | 0.03 | 0.001 |
| RRT 1.19 | 0.10 | 0.09 | 0.09 | 0.09 | 0.10 | 0.10 | 0.01 | 0.01 | 0.01 | 0.001 | 0.01 |
| RRT 1.22~1.23 | 0.08 | 0.09 | 0.08 | 0.07 | 0.09 | 0.08 | 0.01 | 0.003 | 0.01 | 0.01 | 0.0004 |
| RRT 1.27 | 0.10 | 0.10 | 0.09 | 0.10 | 0.10 | 0.09 | 0.002 | 0.01 | 0.0003 | 0.003 | 0.01 |

| Sample Name | Content(%) | | | | | | Percent Vs. Initial (%) | | | | |
|---|---|---|---|---|---|---|---|---|---|---|---|
| | 0 h | 2 h | 4 h | 8 h | 27 h | 52 h | 2 h | 4 h | 8 h | 27 h | 52 h |
| RRT 0.71 | 1.10 | 1.13 | 1.11 | 1.12 | 1.13 | 1.12 | 103 | 101 | 102 | 103 | 102 |

The following acceptance criteria were established for the analytical methods.

Acceptance Criteria for System Suitability/Chromatographic Parameters

These acceptance criteria are for the parameters of specificity, detection limit (LOD), quantitation limit (LOQ) and robustness. For the blank (diluent), the system needs to be clean and stable and no interference peak is to be observed in the blank chromatograms at the retention time of dulcitol. If any interference exists, the interference should be not more than the dulcitol peak in the sensitivity solution. For the sensitivity solution, the signal to noise (S/N) of dulcitol peak in sensitivity solution should be no less than 10. For the correlation (r), the correlation of the logarithmic calibration curve for L-0.2%, L-1% and L-5%#1 (first injection) should be no less than 0.980. For the standard solution, the relative standard deviation (RSD) of Lg (peak area) of dulcitol for the first five initial injections of STD #1 (L-5%#1) should be 5%. The tailing factor of the dulcitol peak in the first injection of STD #1 (L-5%#1) should be 2.0. The recovery of STD #2 (L-5%#2) should be within 95%-105%. For bracketing of the standard solutions, the ratio between the Lg(peak area) of bracketing injection and the average Lg(peak area) of first five injections of STD #1 (L-5%#1) should be within 95%-105%.

These acceptance criteria are for the parameters of linearity, range, precision (repeatability and intermediate), accuracy and solution stability. For the blank (diluent), the system needs to be clean and stable and no interference peak is to be observed in the blank chromatograms at the retention time of dulcitol. If any interference exists, the interference should be not more than the dulcitol peak in the sensitivity solution. For the sensitivity solution, the signal to noise (S/N) of dulcitol peak in sensitivity solution should be no less than 10. For the correlation (r), the correlation of the logarithmic calibration curve for L-0.2%, L-1% and L-3%#1 (first injection) should be no less than 0.980. For the standard solution, the RSD of Lg (peak area) of dulcitol for the first five initial injections of STD #1 (L-3%#1) should be 5%. The tailing factor of dulcitol peak in the first injection of STD #1 (L-3%#1) should be 2.0. The recovery of STD #2 (L-3%#2) should be within 95%-105%. For bracketing of the standard solutions, the ratio between the Lg(peak area) of bracketing injection and the average Lg(peak area) of first five injections of STD #1 (L-5%#1) should be within 95%-105%.

For specificity, there should be no noticeable interference peak observed at the retention time of the DAG peak, DBD and dulcitol in the diluent chromatogram. If any interference peak exists, the interference with the DAG should be not more than the dulcitol peak in the sensitivity solution. The retention time of DAG peak in the sample and standard solution are essentially the same (within ±5%).

For the detection limit (LOD), the signal to noise (S/N) should be not less than 3.

For the quantitation limit (LOQ), the signal to noise (S/N) should be not less than 10.

For linearity and range, the correlation coefficient (r) is to be no less than 0.980.

For accuracy, the mean recovery (n=3) for each level should be within 80%-120%.

For precision and repeatability, at levels of 0.5% and above, the relative standard deviation should be ≤20%.

For intermediate precision, the combined RSD % should be ≤20%.

For robustness, the absolute difference should be not more than 0.2% for an impurity ≤1.0%. For an impurity >1.0%, the relative difference should be controlled within ±20%. No new impurities should be observed. These robustness criteria apply to variations in the ELSD gas pressure and ELSD temperature.

For solution stability, the recovery of the aged solutions should be within 85%-115% of the initial assay. For the sample, the absolute difference should be not more than 0.2% for an impurity 1.0%. For an impurity >1.0%, the result of the aged solution should be within 80%-120% of the initial result. No new impurities ≥0.1% should be observed.

At ambient laboratory conditions, all acceptance criteria were met for time intervals of up to 52 hours. At refrigerated conditions (2-8° C.), all acceptance criteria were met for time intervals of up to 48 hours.

CONCLUSION

The analytical system and method described in this example meets all criteria for sensitivity, precision, robustness, stability, and signal to noise ratio, including the signal to noise ratio at the detection limit. Accordingly, this analytical system and method is useful for the analysis of dianhydrogalactitol and impurities found in preparations of dianhydrogalactitol, including dulcitol, dibromodulcitol, and other impurities.

Methods according to the present invention possess industrial applicability for analysis of dianhydrogalactitol preparations and determination and quantitation of impurities in dianhydrogalactitol preparations.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, and literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled.

Those skilled in the art will recognize, or will be able to ascertain using no more than routine experimentation, many equivalents to the specific embodiments of the invention described. Such equivalents are intended to be encompassed by the following claims.

What is claimed is:

1. An analytical method for analyzing the presence and quantity of impurities present in a preparation of dianhydrogalactitol comprising the steps of:
   (a) analyzing a preparation of dianhydrogalactitol by subjecting the preparation to high performance liquid chromatography using a reversed phase amide column employing amide chemistry in a hydrophilic interaction mode and ethylene bridged hybrid (BEH) technology with elution with a mobile phase gradient wherein a first mobile phase is 100% acetonitrile and a second mobile phase is 100% water to separate dianhydrogalactitol from dulcitol and other contaminants of the preparation; and
   (b) determining the relative concentration of one or more peaks resolved by high performance liquid chromatography that represent compounds other than dianhydrogalactitol itself.

2. The method of claim 1 wherein the method detects and quantitates at least one of: (1) dulcitol; (2) dibromodulcitol; (3) an impurity other than dulcitol; and (4) a degradation product of dianhydrogalactitol.

3. The method of claim 1 wherein the flow rate is from about 0.72 mL/min to about 0.88 mL/min.

4. The method of claim 1 wherein the scheme for elution is (1) 0.00 minutes, 90% of 100% acetonitrile; 10% of 100% water; (2) 3.00 minutes, 90% of 100% acetonitrile; 10% of 100% water; (3) 20.00 minutes, 75% of 100% acetonitrile, 25% of 100% water; (4) 25.00 minutes, 50% of 100% acetonitrile, 50% of 100% water; (5) 30.00 minutes, 50% of 100% acetonitrile, 50% of 100% water; (6) 30.10 minutes, 90% of 100% acetonitrile, 10% of 100% water; and (7) 40.00 minutes, 90% of 100% acetonitrile, 10% of 100% water.

5. The method of claim 1 wherein the injection volume is from about 15 μL to about 35 μL.

6. The method of claim 1 wherein the column temperature is from about 28° C. to about 32° C.

7. The method of claim 1 wherein the run time is about 40 minutes.

8. The method of claim 1 wherein the injector temperature is at about 20° C. to about 22° C.

9. The method of claim 1 wherein the method includes a needle wash with 100% acetonitrile.

10. The method of claim 1 wherein detection is by means of evaporative light scattering (ELSD).

11. The method of claim 10 wherein the evaporative light scattering detection comprises post-column addition of a volatile solvent to enhance evaporation of the aqueous fraction of any mobile phase present.

12. The method of claim 11 wherein the volatile solvent is selected from the group consisting of methanol, ethanol, isopropanol, and acetonitrile.

13. The method of claim 10 wherein the ELSD detection conditions are a temperature from about 36° C. to about 44° C., a gas pressure from about 2.0 bar to about 3.0 bar, and a gain of 7.

14. The method of claim 10 wherein the evaporative light scattering detection is compatible with electrospray LC/MS.

15. The method of claim 14 wherein an electrospray tandem mass spectrometer is installed and connected on-line to an HPLC system with ELSD.

16. The method of claim 15 wherein tandem mass spectral data providing chemical information for each of the impurities and degradation products that may be present in a preparation of dianhydrogalactitol is collected.

17. The method of claim 16 wherein the mass spectroscopy in tandem with HPLC provides molecular ion information and possible chemical structures having a molecular weight consistent with the molecular ion information for each of the observed impurities and degradation products.

18. The method of claim 16 wherein at least one impurity or degradation product is identified by separation by column chromatography followed by at least one purification procedure to yield a solid unknown sample.

19. The method of claim 18 wherein the solid unknown sample is characterized for identification by at least one standard analytical procedure selected from the group consisting of nuclear magnetic resonance (NMR), mass spectroscopy (MS), Fourier transform infrared spectroscopy (FT-IR), elemental analysis, determination of purity by HPLC, and determination of water content by the Karl Fischer titration method.

20. The analytical method of claim 1 further comprising the step of performing preparative HPLC collection of at least one specific substance peak present in a preparation of dianhydrogalactitol.

* * * * *